(12) United States Patent
Smith

(10) Patent No.: US 9,028,403 B2
(45) Date of Patent: May 12, 2015

(54) ACCESS PORT HAVING ROLLABLE PROXIMAL END

(71) Applicant: Covidien LP, Mansfield, MA (US)

(72) Inventor: Robert C. Smith, Middlefield, CT (US)

(73) Assignee: Covidien LP, Mansfield, MA (US)

( * ) Notice: Subject to any disclaimer, the term of this patent is extended or adjusted under 35 U.S.C. 154(b) by 119 days.

(21) Appl. No.: 13/734,093

(22) Filed: Jan. 4, 2013

(65) Prior Publication Data

US 2013/0190574 A1 Jul. 25, 2013

Related U.S. Application Data

(60) Provisional application No. 61/588,294, filed on Jan. 19, 2012.

(51) Int. Cl.
*A61B 1/32* (2006.01)
*A61B 17/02* (2006.01)
*A61B 17/34* (2006.01)

(52) U.S. Cl.
CPC ......... *A61B 17/0218* (2013.01); *A61B 17/3423* (2013.01); *A61B 2017/3443* (2013.01); *A61B 2017/3466* (2013.01)

(58) Field of Classification Search
CPC ........... A61B 17/0218; A61B 17/3423; A61B 17/3431; A61B 2017/3484
USPC .......................... 600/201, 203, 204, 206–209
See application file for complete search history.

(56) References Cited

U.S. PATENT DOCUMENTS

| 3,332,417 | A | * | 7/1967 | Blanford William F et al. ............................. 128/850 |
| 5,514,133 | A | * | 5/1996 | Golub et al. ....................... 606/1 |
| 5,545,179 | A | * | 8/1996 | Williamson, IV ............. 606/213 |
| 5,649,550 | A | | 7/1997 | Crook |
| 5,672,168 | A | * | 9/1997 | de la Torre et al. ................ 606/1 |
| 5,803,921 | A | | 9/1998 | Bonadio |

(Continued)

FOREIGN PATENT DOCUMENTS

| EP | 2044897 A1 | 4/2009 |
| EP | 2238926 A2 | 10/2010 |

(Continued)

OTHER PUBLICATIONS

Extended European Search Report dated Feb. 15, 2013 from corresponding EP Application No. 13151771.6 (8 pgs.).

*Primary Examiner* — Ellen C Hammond
*Assistant Examiner* — Jacqueline Johanas

(57) ABSTRACT

A surgical access device for insertion into an opening in tissue includes an adjustable member at a proximal end which is transitionable between an un-deployed configuration where the adjustable member is rolled up proximally and a deployed configuration where the adjustable member is unrolled distally to allow for the use of the surgical access device in an opening having a larger size than the surgical access device. The surgical access device includes an elongate member which is adapted for insertion into an opening in tissue and including a lumen extending therethrough for the reception of a surgical instrument. An adjustable member extends from a proximal portion of the elongate member and is variable between the un-deployed configuration and the deployed configuration where the adjustable member extends distally from the proximal portion of the elongate member when in the deployed configuration to at least partially surround the elongate member.

7 Claims, 7 Drawing Sheets

(56) References Cited

U.S. PATENT DOCUMENTS

| | | | |
|---|---|---|---|
| 6,033,426 A * | 3/2000 | Kaji | 606/213 |
| 6,033,428 A * | 3/2000 | Sardella | 606/213 |
| 6,048,309 A | 4/2000 | Flom et al. | |
| 6,315,770 B1 * | 11/2001 | de la Torre et al. | 606/1 |
| 6,582,364 B2 * | 6/2003 | Butler et al. | 600/208 |
| 6,814,078 B2 | 11/2004 | Crook | |
| 6,945,932 B1 * | 9/2005 | Caldwell et al. | 600/208 |
| 7,008,377 B2 * | 3/2006 | Beane et al. | 600/207 |
| 7,153,261 B2 * | 12/2006 | Wenchell | 600/208 |
| 7,238,154 B2 * | 7/2007 | Ewers et al. | 600/208 |
| 7,445,597 B2 * | 11/2008 | Butler et al. | 600/208 |
| 7,559,893 B2 * | 7/2009 | Bonadio et al. | 600/208 |
| 7,727,146 B2 | 6/2010 | Albrecht et al. | |
| 7,998,068 B2 * | 8/2011 | Bonadio et al. | 600/208 |
| 8,012,088 B2 * | 9/2011 | Butler et al. | 600/208 |
| 8,187,177 B2 * | 5/2012 | Kahle et al. | 600/208 |
| 8,317,691 B2 * | 11/2012 | Bonadio et al. | 600/208 |
| 8,357,086 B2 * | 1/2013 | Kahle et al. | 600/208 |
| 8,361,109 B2 * | 1/2013 | Cropper et al. | 606/210 |
| 8,388,526 B2 * | 3/2013 | Ewers et al. | 600/208 |
| 8,419,635 B2 * | 4/2013 | Shelton et al. | 600/208 |
| 8,821,390 B2 * | 9/2014 | Kleyman | 600/203 |
| 2003/0014076 A1 * | 1/2003 | Mollenauer et al. | 606/213 |
| 2004/0267096 A1 | 12/2004 | Caldwell et al. | |
| 2005/0020884 A1 * | 1/2005 | Hart et al. | 600/206 |
| 2005/0090717 A1 * | 4/2005 | Bonadio et al. | 600/208 |
| 2005/0192483 A1 * | 9/2005 | Bonadio et al. | 600/208 |
| 2005/0209510 A1 * | 9/2005 | Bonadio et al. | 600/208 |
| 2006/0161050 A1 * | 7/2006 | Butler et al. | 600/208 |
| 2007/0093695 A1 * | 4/2007 | Bonadio et al. | 600/208 |
| 2008/0255519 A1 * | 10/2008 | Piskun et al. | 604/174 |
| 2009/0093752 A1 | 4/2009 | Richard et al. | |
| 2010/0081880 A1 * | 4/2010 | Widenhouse et al. | 600/201 |
| 2010/0081881 A1 * | 4/2010 | Murray et al. | 600/203 |
| 2010/0081882 A1 * | 4/2010 | Hess et al. | 600/203 |
| 2010/0249525 A1 * | 9/2010 | Shelton et al. | 600/208 |
| 2010/0249526 A1 * | 9/2010 | Shelton et al. | 600/208 |
| 2011/0021879 A1 * | 1/2011 | Hart et al. | 600/207 |
| 2011/0066001 A1 * | 3/2011 | Shelton et al. | 600/208 |
| 2011/0082341 A1 * | 4/2011 | Kleyman et al. | 600/206 |
| 2011/0144589 A1 * | 6/2011 | Ortiz et al. | 604/164.03 |
| 2011/0251463 A1 | 10/2011 | Kleyman | |
| 2011/0251464 A1 * | 10/2011 | Kleyman | 600/206 |
| 2011/0251465 A1 * | 10/2011 | Kleyman | 600/208 |
| 2012/0029297 A1 * | 2/2012 | Bonadio et al. | 600/208 |
| 2012/0083660 A1 * | 4/2012 | Okoniewski | 600/207 |
| 2012/0130191 A1 * | 5/2012 | Pribanic | 600/208 |
| 2012/0157781 A1 * | 6/2012 | Kleyman | 600/208 |
| 2012/0157785 A1 * | 6/2012 | Kleyman | 600/208 |
| 2012/0245430 A1 | 9/2012 | Kleyman et al. | |
| 2012/0253136 A1 * | 10/2012 | Rodrigues, Jr. | 600/208 |
| 2012/0283520 A1 | 11/2012 | Kleyman | |
| 2013/0172684 A1 * | 7/2013 | Smith | 600/208 |
| 2013/0225933 A1 * | 8/2013 | Kleyman | 600/208 |

FOREIGN PATENT DOCUMENTS

| | | |
|---|---|---|
| EP | 2374423 A1 | 10/2011 |
| EP | 2502587 A1 | 9/2012 |

* cited by examiner

ACCESS PORT HAVING ROLLABLE PROXIMAL END

CROSS-REFERENCE TO RELATED APPLICATIONS

The present applications claims priority to, and the benefit of, U.S. Provisional Patent Application Ser. No. 61/588,294, filed on Jan. 19, 2012, the entire contents of which are hereby incorporated by reference.

BACKGROUND

1. Technical Field

The present disclosure relates generally to surgical instruments for use with a surgical access portal. More particularly, the present disclosure relates to an access port having an adjustable proximal end which is configured to allow the access port to be used through openings of varying size.

2. Description of Related Art

Increasingly, many surgical procedures are performed through small openings or natural openings in the skin. As compared to the larger openings typically required in traditional procedures, smaller openings result in less trauma to the patient. By reducing the trauma to the patient, the time required for recovery is also reduced. Generally, the surgical procedures that are performed through small openings in the skin are referred to as "endoscopic". If the procedure is performed on the patient's abdomen, the procedure is referred to as "laparoscopic". Throughout the present disclosure, the term "minimally invasive" is to be understood as encompassing both endoscopic and laparoscopic procedures.

During a typical minimally invasive procedure, surgical objects, such as surgical access devices (e.g., trocar and cannula assemblies) or endoscopes, are inserted into the patient's body through the incision in tissue. In general, prior to the introduction of the surgical object into the patient's body, insufflation gas is used to enlarge the area surrounding the target surgical site to create a larger, more accessible work area. Accordingly, the maintenance of a substantially fluid-tight seal is desirable so as to inhibit the escape of the insufflation gas and the deflation or collapse of the enlarged surgical site. In response to this, various access devices with sealing features are used during the course of minimally invasive procedures to provide an access for surgical objects to enter the patient's body. Each of these devices is configured for use through a single incision or a naturally occurring orifice (i.e. mouth, anus, or vagina) while allowing multiple instruments to be inserted through the device to access the working space beyond the device.

However, a continuing need exists for a way to utilize a surgical access portal in incisions or openings of varying size where the size of the opening may be larger than the surgical access portal.

SUMMARY

A surgical access device is disclosed herein for insertion into an opening in tissue including an adjustable member at a proximal end which is transitionable between an un-deployed configuration where the adjustable member is rolled up and a deployed configuration where the adjustable member is un-rolled distally to allow for the use of the access port in an opening having a larger size than the surgical access device.

The surgical access device includes an elongate member which is adapted for insertion into an opening in tissue and includes a lumen extending therethrough for the reception of a surgical instrument. An adjustable member extends from a proximal portion of the elongate member and is variable between an un-deployed configuration and a deployed configuration where the adjustable member extends distally from the proximal portion of the elongate member when in the deployed configuration to at least partially surround the elongate member. The adjustable member is transitionable from the un-deployed configuration to the deployed configuration by unrolling a distal portion of the adjustable member distally.

The distal portion of the adjustable member may include a rounded tip and may be positioned adjacent to an inner surface of tissue when inserted into the opening in tissue. When the adjustable member is in the deployed configuration, a space may be defined between a portion of the elongate member and the adjustable member.

A proximal portion of the adjustable member may extend radially outward from the elongate member and is configured and dimensioned to be positioned adjacent to an outer surface of tissue when the elongate member is inserted into the opening in tissue. A portion of the adjustable member may depend radially inward from the proximal portion of the adjustable member after insertion of the elongate member into the opening in tissue. The adjustable member may be at least slightly biased radially outward when in the deployed configuration.

A surgical access system is also disclosed which includes a sleeve member insertable into an opening in tissue and having a proximal portion and a distal portion. The proximal portion of the sleeve member is adapted to secure the sleeve member to an outer surface of tissue and the distal portion of the sleeve member is adapted to secure the sleeve member to an inner surface of tissue. The sleeve member defines a passage therethrough for the reception of a surgical access device.

The surgical access system also includes an elongate member which is adapted for insertion into the passage of the sleeve member. The elongate member includes a lumen extending therethrough for the reception of a surgical instrument and an adjustable member extending from a proximal portion of the elongate member and being variable between an un-deployed configuration and a deployed configuration. The adjustable member extends distally from the proximal portion of the elongate member when in the deployed configuration.

The adjustable member may include a rounded tip at a distal end which is adapted to seal against the distal portion of the sleeve member and may at least partially surround the elongate member when in the deployed configuration.

The distal portion of the sleeve member may include an anchor member having a wiper extending therefrom. The wiper is adapted to receive a distal end of the adjustable member in a substantially fluid-sealed manner when the elongate member is in the deployed configuration and inserted into the passage of the sleeve member. The adjustable member may be at least slightly biased radially outward when in the deployed configuration to engage the sleeve member and inhibit removal of the elongate member from the opening in tissue.

A method of providing surgical access through an opening in tissue is disclosed, the method includes determining if the opening in tissue is a first smaller size or a second larger size, transitioning an adjustable member of a surgical access device towards an un-deployed configuration if the opening is the first size, transitioning the adjustable member towards a deployed configuration if the opening is the second size, and inserting the surgical access device into the opening in tissue.

The adjustable member remains proximal of the opening in tissue when the adjustable member is in the un-deployed configuration and the surgical access device is inserted into the opening in tissue. When the adjustable member is in the deployed configuration, inserting the surgical access device into the opening in tissue includes inserting the adjustable member into the opening in tissue such that a distal portion of the adjustable member is proximate to an inner surface of tissue.

The method further includes inserting a sleeve into the opening in tissue where inserting the surgical access device into the opening in tissue includes inserting the surgical access device into a passage of the sleeve.

The adjustable member may also include a rounded tip at a distal end where inserting the surgical access device into the passage of the sleeve includes engaging the rounded tip to a wing disposed at a distal portion of the sleeve.

Transitioning the adjustable member towards the un-deployed configuration may include rolling a distal portion of the adjustable member in a proximal direction and transitioning the adjustable member towards the deployed configuration may include unrolling the distal portion of the adjustable member in a distal direction. The adjustable member may be at least slightly biased radially outward when in the deployed configuration.

BRIEF DESCRIPTION OF THE DRAWINGS

The accompanying drawings, which are incorporated in and constitute a part of this specification, illustrate embodiments of the presently disclosed surgical access system, and together with a general description of the disclosed surgical access system given above, and the detailed description of the embodiments given below, serve to explain the principles of the disclosed surgical access system.

DETAILED DESCRIPTION

Figure 1:
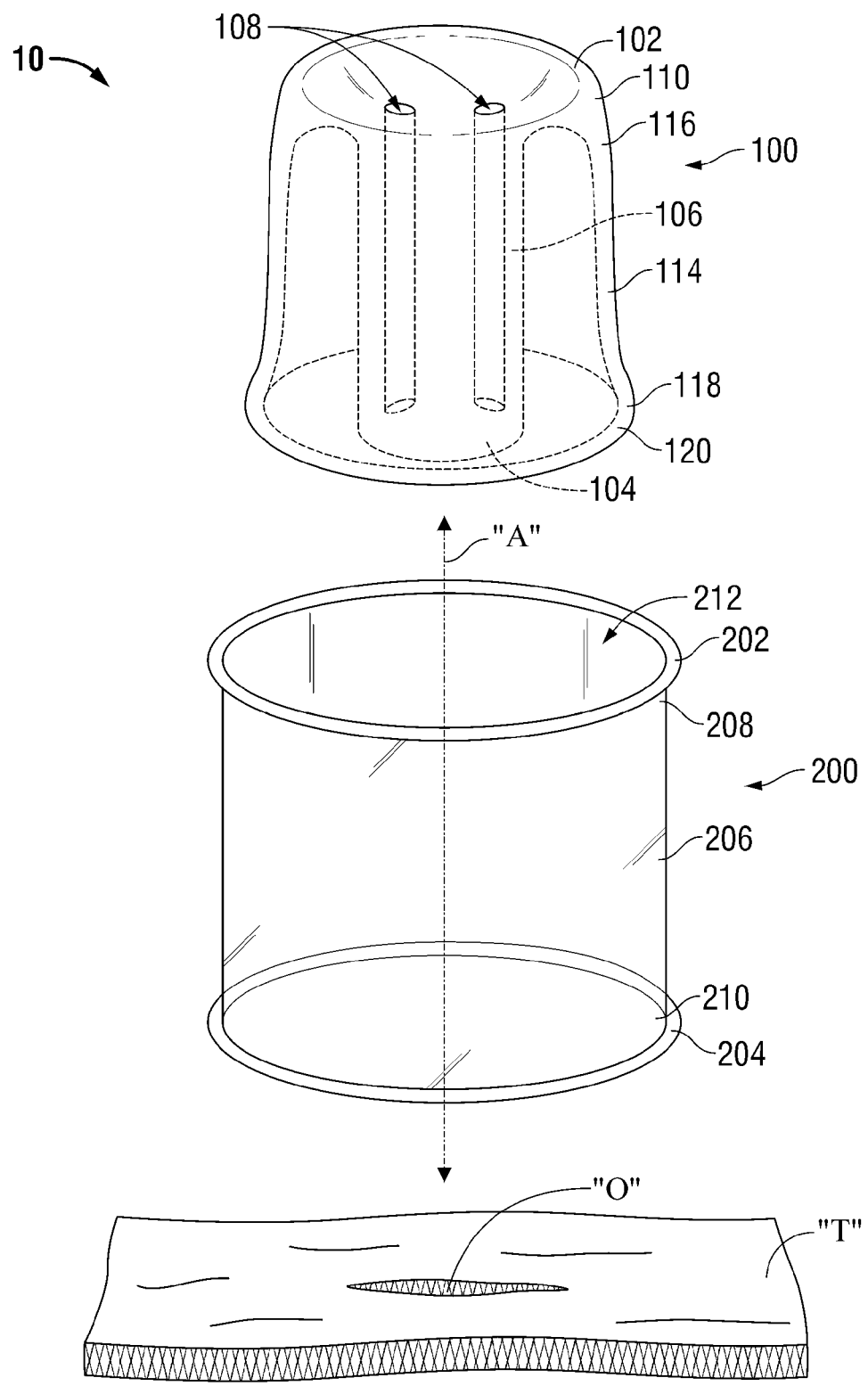
FIG. 1 is perspective view a surgical access system in accordance with the present disclosure.

Various embodiments of the presently disclosed surgical access system, and methods of using the same, will now be described in detail with reference to the drawings wherein like references numerals identify similar or identical elements. In the drawings, and in the following description, the term "proximal" should be understood as referring to the end of the pertinent structure that is closer to the clinician during proper use, while the term "distal" should be understood as referring to the end that is farther from the clinician, as is traditional and conventional in the art. Additionally, use of the term "opening" herein below should be understood to encompass any opening in a patient's tissue, including natural openings (e.g. anus, vagina and mouth) and surgically formed incisions.

Disclosed herein is a surgical access system including an access port having a proximal end which is adjustable to allow the access port to be used through openings or incisions of various sizes. The adjustable proximal end allows a standard sized access port to be used through openings or incisions which may be larger than the standard sized access port. This allows medical staff to use and maintain a single supply of surgical access portals for use with a variety of procedures having openings which would normally require a larger access port.

FIG. 1 illustrates one embodiment of the presently disclosed surgical access system, which is identified by the reference character 10, in use during the course of a minimally invasive surgical procedure. Although described in the context of a laparoscopic surgical procedure herein below, it should be understood that the surgical access system 10 may be utilized during any minimally invasive surgical procedure.

Surgical access system 10 includes an access port 100 and a sleeve 200, each of which will be described in more detail below. Sleeve 200 is adapted for insertion into the opening "O" in tissue "T" prior to insertion of access port 100 to minimize or reduce the effect of access port 100 on the opening "O" and surrounding tissue "T". For example, sleeve 200 allows a surgeon to insert and remove access port 100 or other surgical objects through the opening "O" as necessary and minimizes the exposure of opening "O" to damage or contamination from access port 100. In the absence of an indication to the contrary, it should be understood that the various components of surgical access system 10 are formed from a biocompatible material.

Figure 5:
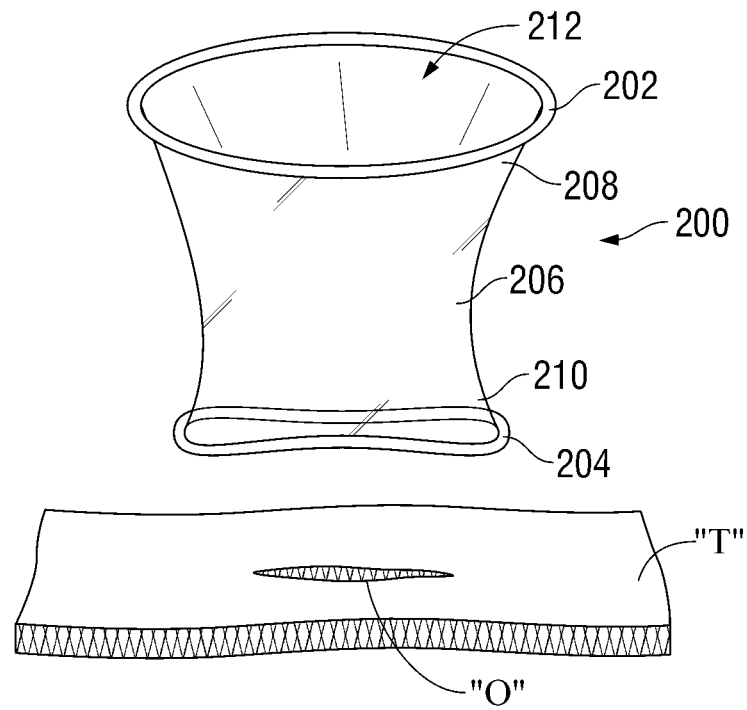
FIG. 5 is a perspective view of the sleeve of the surgical access system of FIG. 1 prior to insertion into an opening in tissue.
Figure 6:
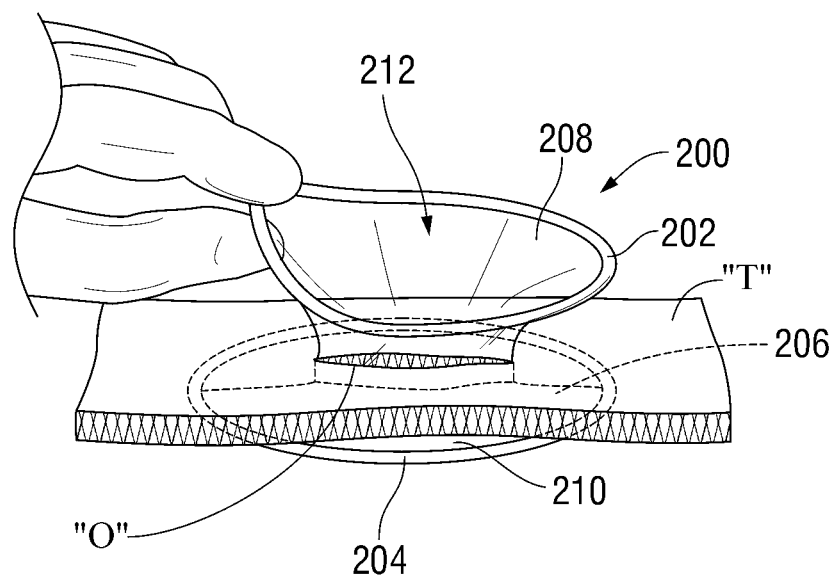
FIG. 6 is a perspective view of the sleeve FIG. 5 after insertion into the opening in tissue.

With reference now to FIGS. 1, 5 and 6, the sleeve 200 is configured and dimensioned for insertion into an opening "O" formed in a patient's tissue "T". The sleeve 200 includes a proximal anchor member 202, a distal anchor member 204, and a sleeve member 206.

The proximal anchor member 202 is configured and dimensioned for engagement with an outer surface of the tissue "T" to inhibit advancement of the proximal anchor member 202 through the opening "O", and to facilitate securement of the sleeve 200 relative to the tissue "T". Although illustrated as substantially annular in configuration, it should be understood that the proximal anchor member 202 may assume any suitable geometrical configuration, such as, for example, an elliptical or rectangular configuration.

In one embodiment of surgical access system 10, sleeve member 206 is movable between an elongated configuration and a shortened configuration via manipulation of the proximal anchor member 202. The proximal anchor member 202 may have a non-circular transverse cross-sectional configuration adapted for maintaining the shortened configuration of the sleeve member 206 by engagement with an outer surface of tissue "T". For example, the transverse cross-sectional configuration may be kidney shaped, crescent shaped, or other shapes suitable to engaging the outer surface of tissue "T".

In one embodiment of the surgical access system 10, the proximal anchor member 202 may be formed from a resilient material that allows for repositioning between an expanded configuration and a compressed configuration. For example, the proximal anchor may be formed from a flexible polymeric material. Alternatively, however, the proximal anchor member 202 may formed from a substantially more rigid material, e.g., an ABS polymer.

Referring again to FIGS. 5 and 6, the distal anchor member 204 is configured and dimensioned for engagement with an internal surface of the tissue "T" to inhibit unintentional withdrawal of the sleeve 200 from the opening "O", and facilitate securement of the sleeve 200 relative to the tissue "T." Although illustrated as substantially annular in configuration, it should be understood that the distal anchor member 204 may assume any suitable geometrical configuration, such as, for example, an elliptical or rectangular configuration.

In one embodiment, for example, it is envisioned that the distal anchor member 204 may be formed from an at least partially resilient material, such as a flexible polymeric material. The resilient material comprising the distal anchor member 204 allows for repositioning of the distal anchor member 204 between an expanded configuration and a compressed configuration that facilitates passage of the distal anchor member 204 through the opening "O" in the tissue "T." The respective proximal and distal anchor members 202, 204 may also be formed from the same material, or from different materials. For example, it is envisioned that the respective proximal and distal anchor members 202, 204 may each be formed from a resilient, flexible material, or that the material comprising the proximal anchor member 202 may be appreciably more rigid than the material comprising the distal anchor member 204.

With continued reference to FIGS. 5 and 6, the sleeve member 206 extends between, and connects, the respective proximal and distal anchor members 202, 204. Specifically, the sleeve member 206 includes a proximal end 208 that is connected to the proximal anchor member 202, and a distal end 210 that is connected to the distal anchor member 204. The sleeve member 206 may be connected to the respective proximal and distal anchor members 202, 204 though any suitable means, e.g., via heat sealing, mechanical connection, or through the use of an adhesive. Alternatively, it is envisioned that the sleeve member 206 may be integrally formed with either, or both, of the respective proximal and distal anchor members 202, 204.

The sleeve member 206 includes a passageway 212 that is configured and dimensioned to receive access port 100 or another surgical instrument or device therethrough. Although illustrated as being substantially cylindrical in configuration in FIG. 1, it is envisioned that the sleeve member 206 may assume any suitable geometrical configuration. For example, it is envisioned that the sleeve member 206 may have an hourglass configuration, or that the sleeve member 206 may be elliptical in configuration, as seen in FIGS. 5 and 6.

In one embodiment of surgical access system 10, it is envisioned that the material comprising the sleeve member 206 may be impermeable to fluids and/or bacteria, whereby the sleeve member 206 forms a substantially fluid-tight seal with the opening "O" in the tissue "T." Alternatively, however, it is envisioned that the sleeve member 206 may be adapted to facilitate the communication of fluid therethrough, either by the material of construction, or by the inclusion of one or more openings therein.

Additionally, although not described as such herein below, it is envisioned that either or both of the respective proximal and distal anchor members 202, 204 of the sleeve 200 may be adapted for inflation via the inclusion of an internal space that is adapted to receive a fluid communicated from an external source, e.g., through an inflation port.

Figure 4A:
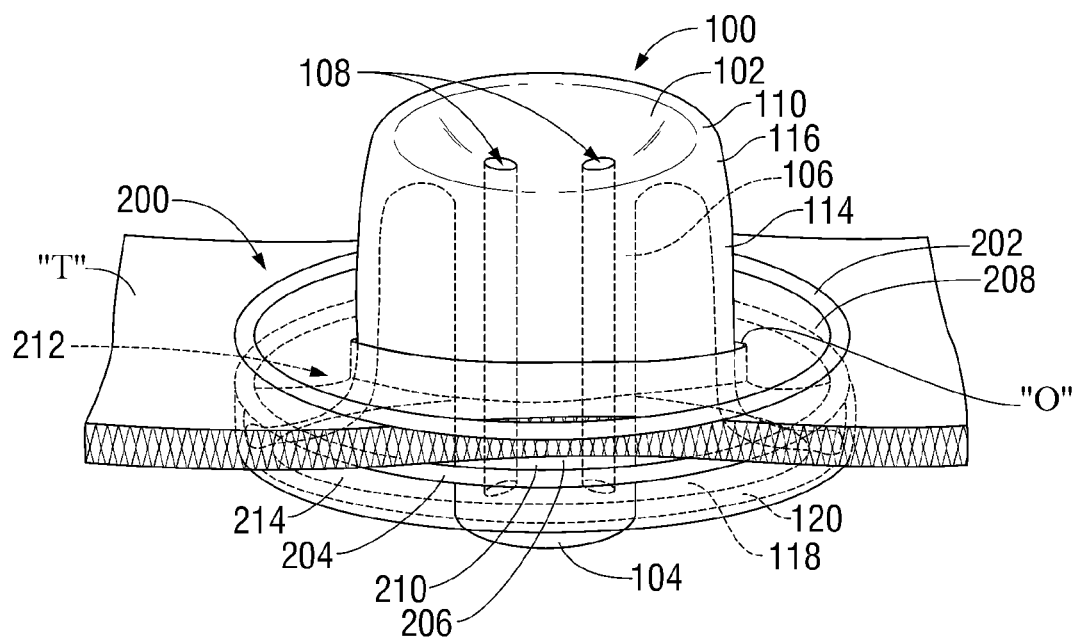
FIG. 4A is a perspective view of the surgical access system of FIG. 1 inserted into an opening in tissue with the adjustable member of the access port in the deployed configuration.
Figure 4B:
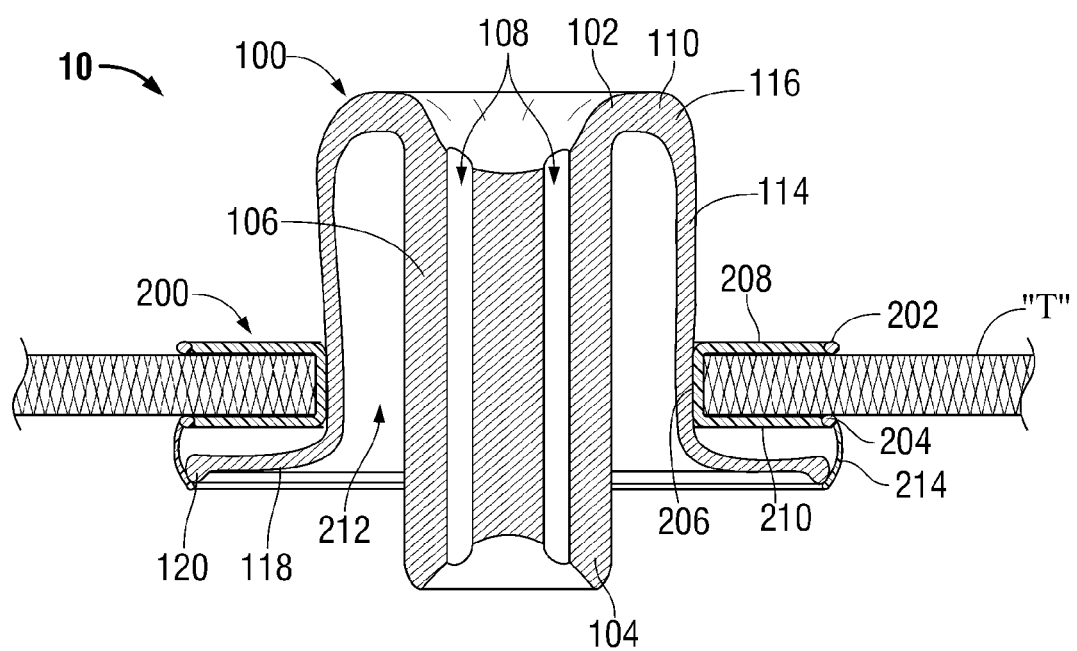
FIG. 4B is a side cross-sectional view of the surgical access system of FIG. 4A.

Referring to FIGS. 4A and 4B, sleeve 200 may further include a wiper 214 extending from distal anchor member 204 for receiving a portion of access port 100 as will be described in more detail below. Wiper 214 may be a separate material extending from or attached to distal anchor member 204 or sleeve member 206 may alternatively extend past distal anchor member 204 to form wiper 214.

Figure 2A:
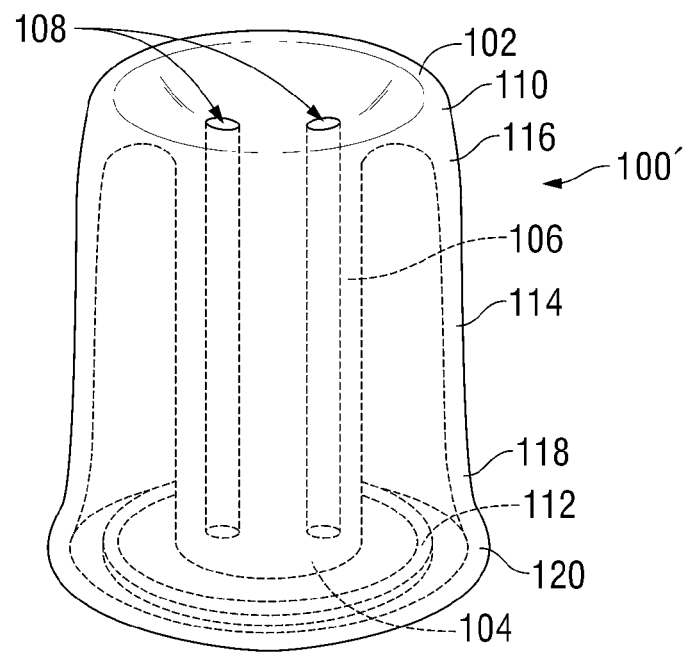
FIG. 2A is a perspective view of an alternate embodiment of an access port having a distal anchor member and showing the adjustable portion of access port in the deployed configuration.
Figure 2B:
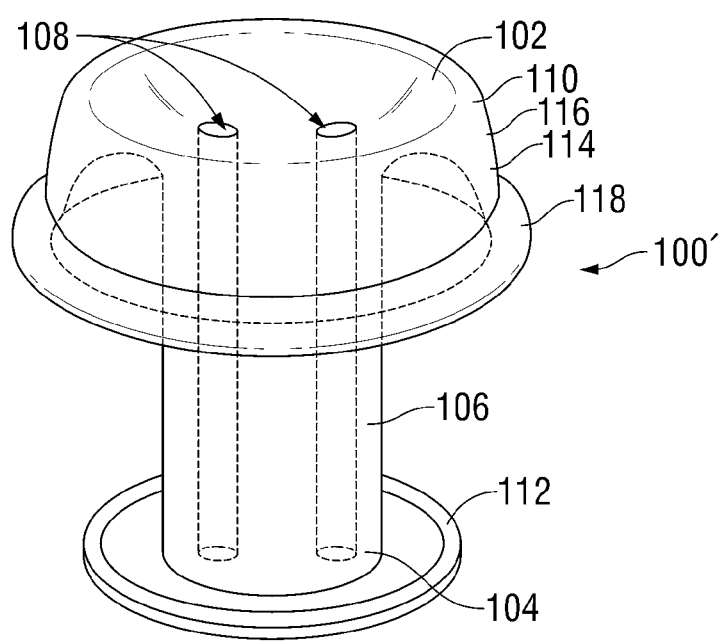
FIG. 2B is a perspective view of FIG. 2A with the adjustable portion in the un-deployed configuration.

Referring now to FIGS. 1, 2A and 2B, the access port 100 is configured and dimensioned for insertion into the passageway 212 of sleeve 200 or directly into the opening "O" in tissue "T". The access port 100 includes a proximal end 102, a distal end 104, and a central portion 106 that is disposed between the respective proximal and distal ends 102, 104. In the illustrated embodiment, the access port 100 further includes one or more lumens 108 that extend longitudinally through the access port 100 between the respective proximal and distal ends 102, 104.

The access port 100 may be formed from any suitable, deformable material that facilitates reconfiguration of the access port 100 in the manner detailed below. For example, it is envisioned that the access port 100 may be formed from a foam material, e.g., polyisoprene or a "memory" foam, having sufficient compliance to form a seal about one or more surgical objects, shown generally as surgical object "I" (FIG. 7B), upon insertion, as described in co-pending U.S. patent application Ser. No. 12/244,024, the entire contents of which are incorporated by reference herein. In such embodiments, the compliancy of the foam material comprising the access port 100 accommodates off axis motion of the surgical object "I."

The proximal end 102 of the access port 100 defines a first transverse dimension and the distal end 104 defines a second transverse dimension. In one embodiment of the access port 100, it is envisioned that the respective first and second transverse dimensions of the proximal and distal ends 102, 104 may be substantially equivalent, as seen in FIGS. 2A, 2B, 3A and 3B, for example. It is also envisioned, however, that the respective transverse dimensions of the proximal and distal ends 102, 104 may be different, as seen in FIGS. 4A and 4B, for example.

As depicted in FIG. 1, the proximal end 102 of the access port 100 defines a generally arcuate surface while the distal end 104 of the access port 100 defines a substantially planar surface. However, embodiments of the access port 100 are also contemplated herein in which either, or both, of the respective proximal and distal ends 102, 104 define surfaces that are substantially planar, or define surfaces that are substantially arcuate to facilitate insertion of the access port 100 into the passageway 212 of sleeve 200 or the opening "O" in tissue "T".

The central portion 106 defines a generally cylindrical shape (FIG. 1), and extends longitudinally between the respective proximal and distal ends 102, 104 of the access port 100. It is envisioned, however, that the central portion 106 may vary along the longitudinal axis "A" of the access port 100 to define, for example, an hourglass shape to facilitate insertion into the sleeve 200 or opening "O" in tissue "T".

Figure 3A:
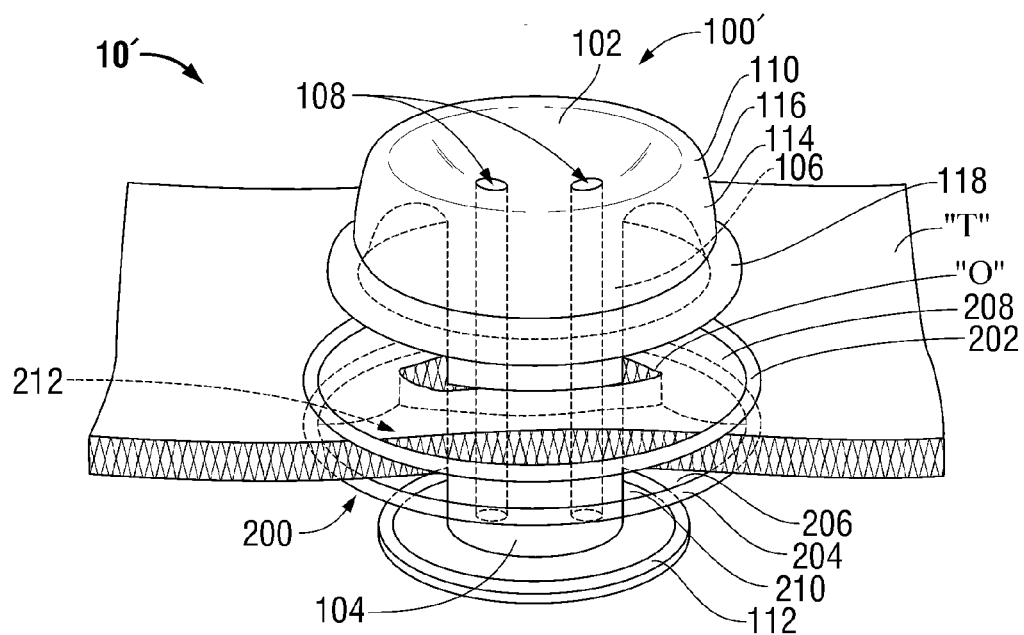
FIG. 3A is a perspective view of the access port of FIG. 2A inserted into a sleeve member and an opening in tissue with the adjustable member of the access port in the un-deployed configuration.
Figure 3B:
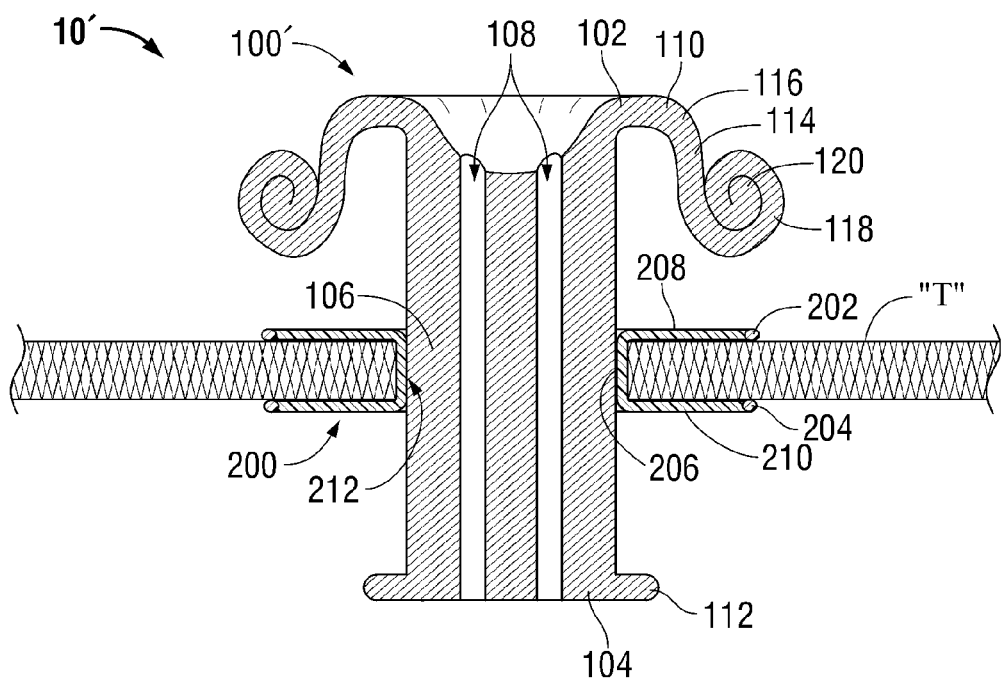
FIG. 3B is a side cross-sectional view of the surgical access system of FIG. 3A.

In the particular embodiment of the access port 100 seen in FIG. 1, transverse dimension of the central portion 106 is appreciably less than one or both of the respective transverse dimensions of the proximal and distal ends 102, 104. For example, as seen in FIG. 1, the transverse dimension of the central portion 106 is substantially less than the transverse dimension of proximal end 102 while the transverse dimension of central portion 106 is substantially equivalent to distal end 104. Alternatively, as seen in FIGS. 3A and 3B, the transverse dimension of the central portion 106 is appreciably less than that of proximal and distal ends 102 and 104. In cross section, it is envisioned that the central portion 106 may exhibit any suitable geometrical configuration, e.g., substantially circular, oval, or oblong.

Figure 7A:
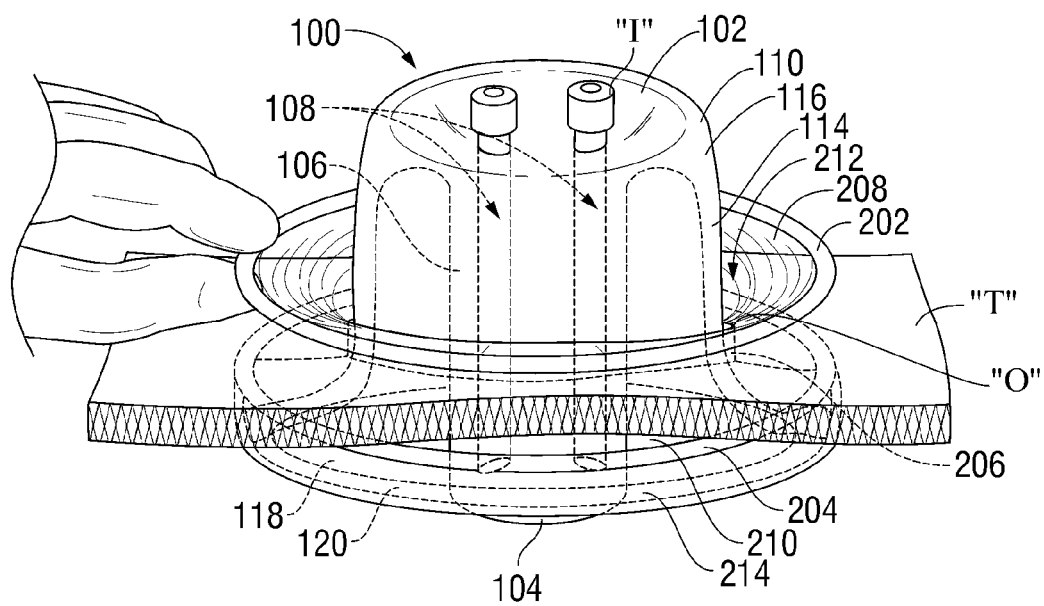
FIG. 7A is a perspective view of the surgical access system of FIG. 1 inserted into an opening in tissue showing the proximal anchor member of the sleeve being rotated.
Figure 7B:
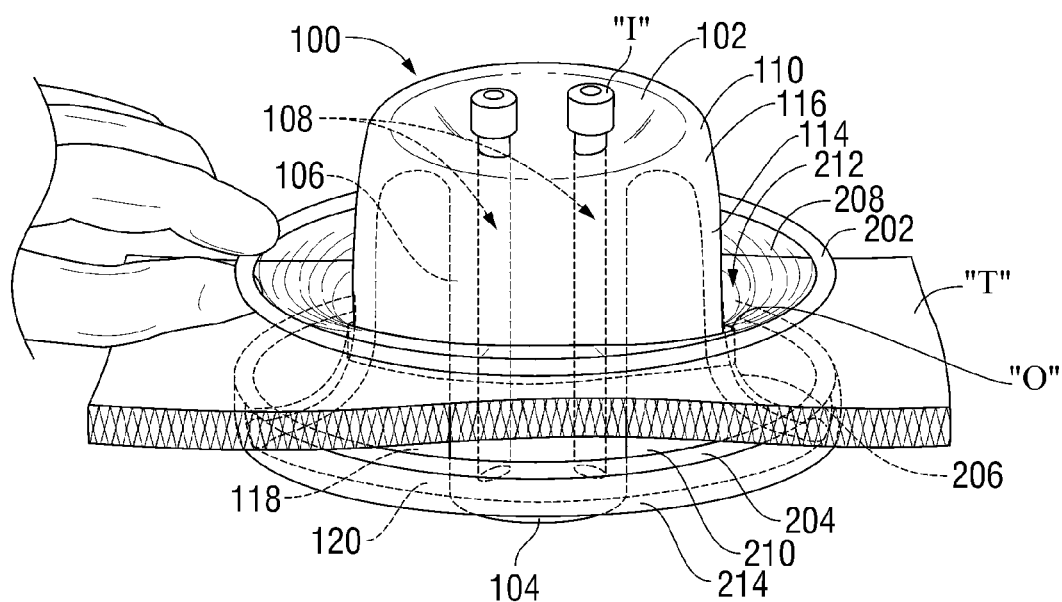
FIG. 7B is a perspective view of the surgical access system of FIG. 7A after the sleeve has been rotated showing the sleeve member of the sleeve pressing against the access port.

With reference now to FIGS. 7A and 7B, each of the lumens 108 extending through the access port 100 is configured to removably receive the surgical object "I". For example, a cannula or other sealing member may be inserted into each of lumens 108 to provide a fluid-tight barrier or seal. The cannula or other sealing member may include any type of seal or valve suitable to maintaining a fluid-tight barrier within the lumen 108 including, for example, a duck-bill valve, a zero closure seal, a septum seal, or a slit. Surgical instruments may then be inserted into and removed from the cannula or other sealing member during the course of a surgical operation with minimal loss of insufflation gas (not shown) or other fluids from the surgical site.

Alternatively, lumens 108 may form a seal directly with a surgical instrument or object "I" inserted therethrough or may include a sealing valve for maintaining a fluid-tight barrier when no surgical object or instrument "I" is inserted. For example, prior to the insertion of the surgical object "I", the lumen 108 may be in a first state, in which the lumen 108 defines an initial transverse dimension which is smaller than the surgical object "I". Upon insertion of the surgical object "I," however, the lumen 108 is expanded into a second state, wherein the lumen 108 defines a second, larger transverse dimension which substantially approximates the outer transverse dimension of the surgical object "I" such that a substantially fluid-tight seal is formed between the lumen 108 and the surgical object "I" in order to substantially prevent the escape of insufflation gas (not shown) through the lumen 108.

It is envisioned that the lumen(s) 108 may be configured as a slit, i.e., wherein the initial transverse dimension is approximately equal to zero, such that the escape of insufflation gas (not shown) through each lumen 108 is substantially prevented in the absence of the surgical object "I". Alternatively, however, it is envisioned that the lumen 108 may define an aperture that is open in the initial state, i.e., wherein the initial transverse dimension is greater than zero.

In addition, it is envisioned that the access port 100 may be devoid of lumens 108, and that advancement of the surgical object(s) "I" through the material comprising the surgical access port 100 may create an opening in the access port 100. In such embodiments, the material comprising the access port 100 may be flowable in nature, or sufficiently compliant to permit such insertion. For example, it is envisioned that the access port 100 may be formed from an open-cell polyurethane foam, a thermoplastic elastomer (TPE), or a gel. It is further envisioned that formation of the access port 100 may involve a process whereby an inert gas, such as $CO_2$ or nitrogen, is infused into the material so as to form a foam structure. A lubricious coating, such as parylene N or C, may be applied to internal surfaces of the lumens 108 in order to facilitate insertion of the surgical object "I" through the access port 100.

The deformable material comprising the access port 100 allows at least a portion of access port 100 to be compressible between an expanded configuration and a compressed configuration in order to facilitate insertion, and securement, of the access port 100 within the passageway 212 of sleeve 200 or opening "O" in tissue "T". For example, prior to insertion, distal end 104 may be compressed such that the transverse dimension of the distal end 104 is smaller than the passageway 212 of sleeve 200 or opening "O" in tissue "T" to allow distal end 104 to be inserted into the passageway 212 or opening "O" in tissue "T". Central portion 106 may also be compressed if necessary for insertion into the passageway 212 of sleeve 200 or opening "O" in tissue "T".

One or more anchor members 110 and 112 may be associated with either, or both, of the respective proximal and distal ends 102, 104 of the access port 100. For example, in an alternate embodiment of the present disclosure, as shown in FIGS. 2A, 2B, 3A and 3B, a surgical access system 10' is shown including an access port 100' which is similar to access port 100. Access port 100' has a proximal anchor member 110 extending from proximal end 102 which may be used to assist in inhibiting over insertion of access port 100' through the passageway 212 of sleeve 200 or opening "O" in tissue "T" by abutting or pressing against the proximal end 208 of sleeve member 206 or outer surface of tissue "T" and a distal anchor member 112 extending from distal end 104 which may be used to inhibit removal of access portal 100' from the passageway 212 of sleeve 200 or opening "O" after inserted by abutting or pressing against the distal end 210 of sleeve member 206 or an inner surface of tissue "T". Sleeve member 206 may, for example, be disposed between anchor members 110 and 112 and the inner and outer surfaces of tissue "T" respectively.

A wiper (not shown) similar to wiper 214 of FIGS. 4A and 4B may be provided to engage or receive distal anchor member 112 to assist in securing access port 100' within sleeve 200 or opening "O" in tissue "T". Proximal anchor member 202 of sleeve 200 may be manipulated to transition sleeve member 200 towards the shortened configuration to further engage the wiper with the distal anchor member 112 to further secure anchor member 100' within passageway 212. The anchor members 110 and 112 may be composed of any suitable biocompatible material that is at least semi-resilient to allow for resilient deformation of the anchor members 110 and 112. Additionally, although shown as substantially annular in configuration, it is envisioned that the anchor members 110 and 112 may assume any other suitable geometrical configuration, such as, for example, an oval, a square or a triangle. It is contemplated that either of access ports 100 and 100' may include both proximal anchor member 110 and distal anchor member 112, may include only one of proximal anchor member 110 and distal anchor member 112, or may include no anchor members.

As seen in FIGS. 1, 2A, 2B, 3A, 3B, 4A, and 4B, proximal anchor member 110 may further include an adjustable member 114 which is transitionable between a first or un-deployed configuration (FIGS. 2B, 3A and 3B) and a second or deployed configuration (FIGS. 1, 2A, 4A and 4B) to allow for the insertion of access port 100 into openings of varying size. Access port 100 may be monolithically formed with central portion 106 and adjustable member 114 being a unitary structure. For example, adjustable member 114 may have a proximal portion 116 and a distal portion 118 where the distal portion 118 is adapted to be rolled up proximally toward the proximal portion 116 (FIG. 3B) when the adjustable member 114 is transitioned from the deployed configuration to the un-deployed configuration. In this way when adjustable member 114 is in the un-deployed configuration (FIGS. 3A and 3B), adjustable member 114 defines a reduced profile such that adjustable member 114 does not impede the surgeons use of access port 100 and access port 100 may be inserted into an opening having a smaller or "standard" size as described above, such as, e.g. an opening which is about two to three millimeters. When in the deployed configuration (FIGS. 4A and 4B), the distal portion 118 of adjustable member 114 is unrolled distally such that it extends distally from proximal portion 116 and at least partially surrounds at least a portion of the length of access port 100. When in the deployed configuration, adjustable member 114 is adapted to engage sleeve member 206 adjacent to an inner surface of tissue "T", as seen in FIGS. 4A and 4B, or to engage the inner surface of tissue "T" itself to secure access port 100 within an incision or opening "O" in tissue "T" which has a larger size than access port 100, e.g. an opening which is about three to seven millimeters. When access port 100 is inserted into an opening "O" in tissue "T" which has a larger size than access port 100 it may not be necessary to transition the access port 100 to the compressed configuration for insertion.

Adjustable member 114 may form a substantially fluid-tight seal the opening "O" or with sleeve 200 and may also be at least slightly biased radially outwards when in the deployed configuration to facilitate engagement of distal portion 118 with the sleeve member 206 and distal anchor member 204 of sleeve 200 or inner surface of tissue "T". A portion of the adjustable member 114 may be spaced from access port 100 when adjustable member 114 is in the deployed configuration, as seen in FIG. 4B.

Distal portion 118 includes a tip 120 at a distal end which is adapted for engaging sleeve 200 in a substantially fluid-tight manner. For example, tip 120 may be rounded (FIG. 4B) or may define a cross section which is substantially circular. Alternatively tip 120 may define a cross section which defines other shapes such as a crescent, kidney or any other suitable shape for engaging distal portion 118 to sleeve 200 after insertion. For example, tip 120 may engage wiper 214 of sleeve 200 to form a substantially fluid-tight seal with sleeve 200. Wiper 214 may removably secure distal portion 118 and tip 120 of access port 100 to secure access port 100 within the passageway 212 of sleeve 200 and within the opening "O" in tissue "T" and to inhibit unintentional withdrawal of access port 100 from the opening "O" in tissue "T". Proximal anchor member 202 of sleeve 200 may be manipulated to transition sleeve member towards the shortened configuration to further engage wiper 214 with the distal portion 118 and tip 120 to further secure access port 100 within sleeve 200 after access port 100 has been inserted into passageway 212 of sleeve 200 and the opening "O" in tissue "T". Wiper 214 may also serve to inhibit over insertion of access port 100 through passageway 212 when distal portion 118 and tip 120 are engaged with wiper 214 by preventing further insertion of adjustable member 114 into passageway 212. Tip 120 may be formed of a material which is more resilient than distal portion 118 to provide a degree of rigidity when engaging sleeve 200 or wiper 214.

Adjustable member 114 may be formed of an at least partially resilient material, such as, for example, a flexible polymeric material, may be formed at least partially of a substantially more rigid material, such as, for example, an ABS polymer. It is also contemplated that different portions of adjustable member 114 may be formed of different materials. For example, proximal portion 116 and distal portion 118 may be formed of the same material or may be formed of different materials where, for example, proximal portion 116 is substantially more rigid than distal portion 118.

Figure 8A:
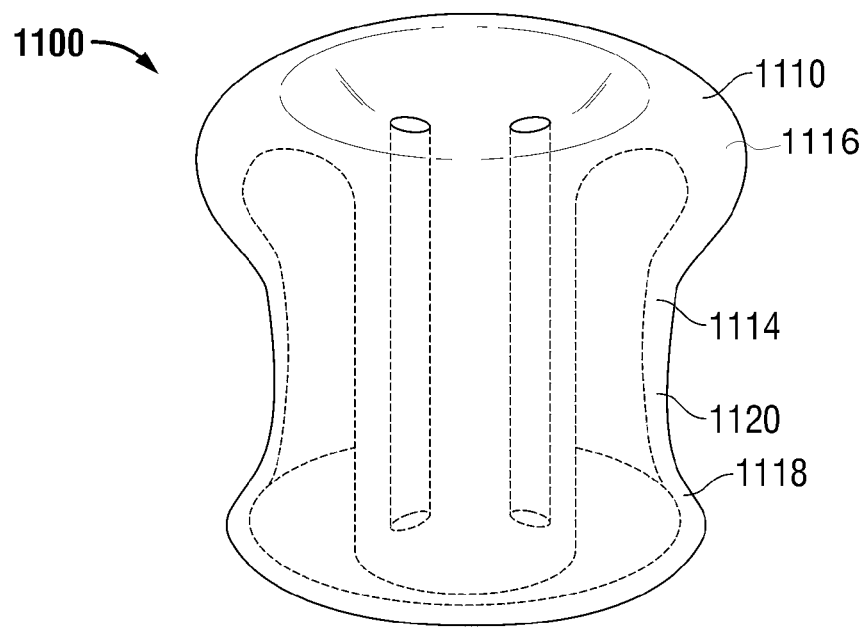
FIG. 8A is a perspective view of an access port of a surgical access system according to an another embodiment of the present disclosure.
Figure 8B:
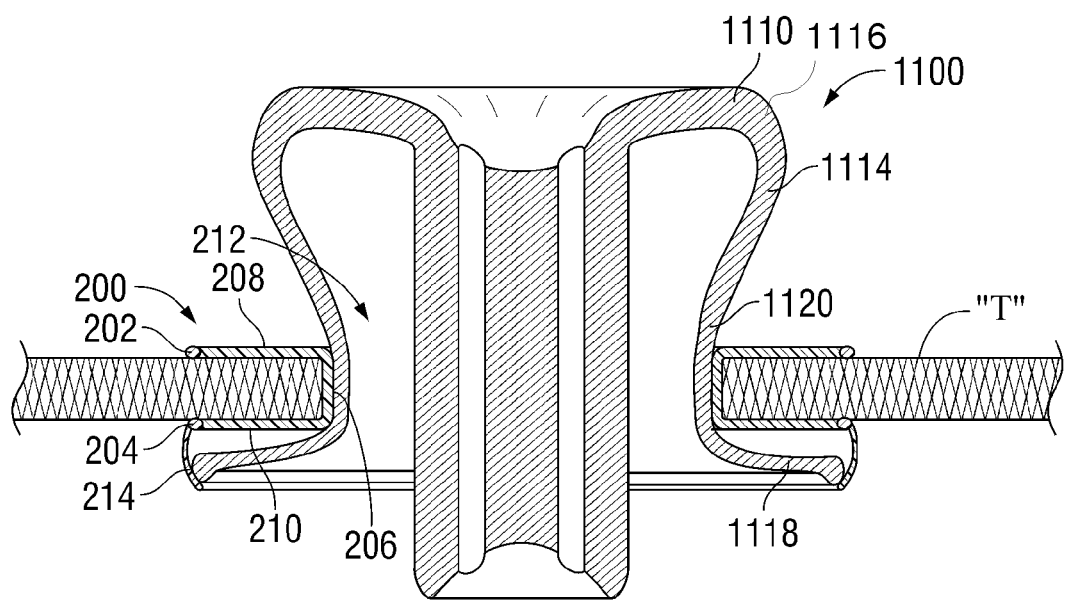
FIG. 8B is a side cross-sectional view of the surgical access port of FIG. 8A inserted into a sleeve.

In one embodiment which is similar to the previous embodiment wherein like numerals identify similar elements, as seen in FIGS. 8A and 8B, an access port 1100 includes an adjustable member 1114 having a proximal portion 1116 which may be formed of a substantially more rigid material than a distal portion 1118 where, for example, proximal portion 1116 extends radially outward from a proximal anchor 1110 of access port 1100 and may have a transverse dimension which is equal to or larger than the incision or opening "O". Distal portion 1118 extends distally from proximal portion 1116 to engage sleeve 200 or the inner surface of tissue "T" as described above. In this way when distal portion 1118 is engaged with sleeve 200 or the inner surface of tissue "T", distal portion 1118 depends radially inward from the proximal portion to define a substantially arcuate curvature with a central portion 1120 engaging sleeve member 206 or a side of opening "O" to further secure access port 1100 within the opening "O".

With reference now to FIGS. 2A, 2B, 3A, 3B, 4A, 4B, 5, 6, 7A and 7B, the use and function of the surgical access system 10 will be discussed. During the course of a typical minimally invasive procedure, the internal worksite is insufflated with a suitable biocompatible gas, e.g., $CO_2$, such that the internal walls of the worksite are raised and lifted away from the organs and tissue housed therein. The insufflation may be performed with an insufflation needle or similar device, as is conventional in the art.

The distal anchor member 204 of the sleeve 200 is prepared for insertion into the opening "O" in tissue "T" by transitioning distal anchor member 204 from the expanded configuration to the compressed configuration. Once in the compressed configuration, distal anchor member 204 is inserted into the opening "O" formed in the tissue "T" and is allowed to return to the expanded configuration where distal anchor member 204 is expanded beneath the tissue "T" to engage the inner surface of tissue "T", as seen in FIGS. 5 and 6.

The sleeve 200 is arranged according to the illustrations provided in FIGS. 3B and 4B, whereby the distal anchor member 204 is positioned beneath (distally of) the tissue "T," and the proximal anchor member 202 is positioned above (proximally of) the tissue "T," so as to facilitate anchoring of the sleeve 200 within the opening "O." Proximal anchor member 202 is then manipulated to move or transition the sleeve member 206 between the elongated configuration and the shortened configuration as necessary depending on the size of the opening "O" in tissue "T". For example, in a large opening "O" proximal anchor member 202 may be manipulated toward the elongated configuration to increase the length of sleeve member 206 while in a smaller opening "O" proximal anchor member 202 may be manipulated toward the shortened configuration to decrease the length of sleeve member 206. Proximal anchor member 202 may be rotated or rolled about itself to increase or decrease the length of sleeve member 206 where sleeve member 206 may be wrapped around proximal anchor member 202. In this way the sleeve 200 may be adjusted to fit any size of opening "O" in a patient's tissue "T".

Once sleeve 200 is secured in opening "O", access port 100 is inserted into the passageway 212 of sleeve 200 as described above and shown in FIGS. 3B and 4B. When the opening "O" in tissue "T" is a small or "standard size", adjustable member 114 is transitioned to the un-deployed configuration (FIG. 2B) prior to insertion by rolling the distal portion 118 of adjustable member 114 proximally. The distal end 104 and central portion 106 of access port 100 are then inserted into the passageway 212 of sleeve 200 (FIGS. 3A and 3B) while the adjustable member 114 remains proximal of the passageway 212. When the opening "O" in tissue "T" is larger than access port 100, adjustable member 114 is transitioned to the deployed configuration (FIG. 2A) prior to insertion by unrolling the distal portion 118 of adjustable member 114 distally to extend adjustable member 114 distally. The distal portion 118 of adjustable member 114 and the distal end 104 and central portion 106 of access port 100 are then inserted into the passageway 212 of sleeve 200 with distal portion 118 of adjustable member 114 abutting or pressing against sleeve member 206 and/or distal anchor member 204 of sleeve 200 to form a substantially fluid-tight seal therewith (FIGS. 4A and 4B). As seen in FIGS. 4A and 4B, distal portion 118 may also engage wiper 214 of sleeve 200 to assist in securing access port 100 within the opening "O" in tissue "T" and to assist in forming a substantially fluid-tight seal with sleeve 200.

After access port 100 has been inserted into the opening "O" in tissue "T", proximal anchor member 202 of sleeve 200 may be rotated relative to distal anchor member 204 to twist or at least partially rotate sleeve member 206 about access port 100, as illustrated in FIGS. 7A and 7B. Rotating proximal anchor member 202 relative to distal anchor member 204 winds sleeve 200 about the access port 100 to further facilitate formation of a substantially fluid-tight seal and also assists in securing the access member within the passageway 212 of sleeve 200.

A surgeon may then insert surgical instruments "I" into lumens 108 of access port 100 to perform the surgical operation.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to the precise embodiments described herein, and that various other changes and modifications may be effected by one skilled in the art without departing from the scope or spirit of the present disclosure.

What is claimed is:

1. A surgical access system comprising:
    a sleeve member insertable into an opening in tissue, the sleeve member including a proximal portion and a distal portion, the proximal portion adapted to secure the sleeve member to an outer surface of tissue and the distal portion adapted to secure the sleeve member to an inner surface of tissue, the sleeve member defining a passage therethrough for the reception of a surgical access device; and
    a monolithic access port comprising an elongate member and an adjustable member,
        the elongate member adapted for insertion into the passage of the sleeve member, the elongate member including a lumen extending therethrough for reception of a surgical instrument; and
        the adjustable member extending from a proximal portion of the elongate member and being variable between an un-deployed configuration and a deployed configuration, the adjustable member extending distally from the proximal portion of the elongate member when in the deployed configuration, such that a distal portion of the adjustable member is insertable into the sleeve member adjacent to the inner surface of tissue.

2. A surgical access system according to claim 1, wherein the adjustable member includes a rounded tip at a distal end, the rounded tip adapted to seal against the distal portion of the sleeve member.

3. A surgical system according to claim 1, wherein the adjustable member at least partially surrounds the elongate member when in the deployed configuration.

4. A surgical access system according to claim 1, wherein the distal portion of the sleeve member includes an anchor member having a wiper extending therefrom, the wiper adapted to receive a distal end of the adjustable member in a substantially fluid-sealed manner when the elongate member is in the deployed configuration and inserted into the passage of the sleeve member.

5. A surgical access system according to claim 1, wherein the adjustable member is at least slightly biased radially outward when in the deployed configuration to engage the sleeve member and inhibit removal of the elongate member from the opening in tissue.

6. A surgical access system according to claim 1, wherein a space is defined between a portion of the elongate member and the adjustable member with the adjustable member in the deployed configuration.

7. A surgical access system according to claim 1, wherein a distal portion of the adjustable member is flared out radially in the deployed configuration.

* * * * *